(12) United States Patent
Mueller

(10) Patent No.: US 11,740,169 B2
(45) Date of Patent: Aug. 29, 2023

(54) METHOD FOR MEASURING COUNTING RATES OR MEASURED VARIABLES DEPENDENT ON THE COUNTING RATES AND APPARATUS FOR MEASURING COUNTING RATES OR MEASURED VARIABLES DEPENDENT ON THE COUNTING RATES

(71) Applicant: Berthold Technologies GmbH & Co. KG, Bad Wildbad (DE)

(72) Inventor: Steffen Mueller, Pforzheim (DE)

(73) Assignee: Berthold Technologies GmbH & Co. KG, Bad Wildbad (DE)

( * ) Notice: Subject to any disclaimer, the term of this patent is extended or adjusted under 35 U.S.C. 154(b) by 74 days.

(21) Appl. No.: 17/342,705

(22) Filed: Jun. 9, 2021

(65) Prior Publication Data
US 2021/0389220 A1    Dec. 16, 2021

(30) Foreign Application Priority Data
Jun. 10, 2020  (EP) .................................... 20179370

(51) Int. Cl.
G01N 9/24 (2006.01)
G01N 23/095 (2018.01)
G01N 23/10 (2018.01)

(52) U.S. Cl.
CPC ............. G01N 9/24 (2013.01); G01N 23/095 (2018.02); G01N 23/10 (2013.01)

(58) Field of Classification Search
CPC ........ G01N 9/24; G01N 23/10; G01N 23/095; G01N 23/06; G01N 33/2823
See application file for complete search history.

(56) References Cited

U.S. PATENT DOCUMENTS 7,180,054 B2    2/2007  Nistor
2019/0078916 A1  3/2019  Chazal et al.

FOREIGN PATENT DOCUMENTS

| EP | 3 264 078 A1 | 1/2018 |
|---|---|---|
| GB | 2569322 A | 6/2019 |
| WO | WO 03/052396 A2 | 6/2003 |

*Primary Examiner* — Jurie Yun
(74) *Attorney, Agent, or Firm* — Crowell & Moring LLP

(57) ABSTRACT

A method for measuring counting rates or measured variables dependent on the counting rates for determining a density profile of at least two substances with different densities arranged within a container by using a plurality of detectors is provided. The method includes recording respective gamma rays which have penetrated at least partially through at least one of the substances by using the detectors, and generating a respective counting rate or a respective measured variable dependent on the counting rate only on the basis of respectively recorded gamma rays of which the respective gamma energy is greater than or equal to an energy threshold value, the energy threshold value being a minimum of 0.5 times a Compton energy value of a Compton gap of the gamma rays.

15 Claims, 4 Drawing Sheets

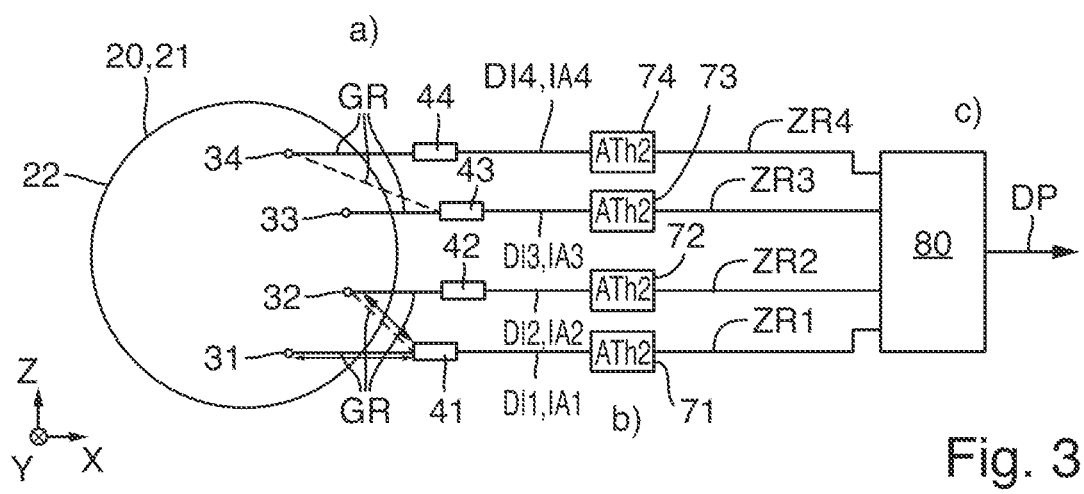
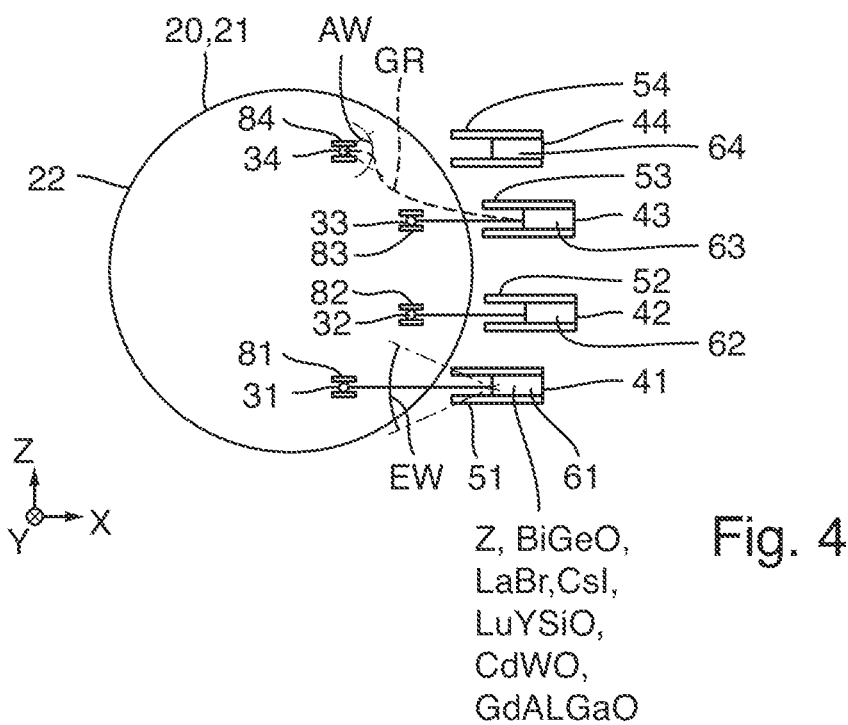

METHOD FOR MEASURING COUNTING RATES OR MEASURED VARIABLES DEPENDENT ON THE COUNTING RATES AND APPARATUS FOR MEASURING COUNTING RATES OR MEASURED VARIABLES DEPENDENT ON THE COUNTING RATES

CROSS REFERENCE TO RELATED APPLICATION

This application claims priority under 35 U.S.C. § 119 from European Patent Application No. 20179370.0, filed Jun. 10, 2020, the entire disclosure of which is herein expressly incorporated by reference.

BACKGROUND AND SUMMARY OF THE INVENTION

The invention relates to a method and an apparatus for measuring counting rates or measured variables dependent on the counting rates, in particular for process metrology.

Such methods and apparatuses can be used for example in multi-level measurements, with which filling levels of multiple liquids in a tank can be radiometrically measured or recorded. A frequent application for this is for example an oil-water separator in the oil industry. For example, a mixture of oil, water, sand and gas is introduced into the separator, and then the separator is intended to separate the mixture by way of gravitation, so that the individual liquids can be drained off separately. The more precise the individual filling levels are, the more efficiently and cost-effectively the separator can be operated.

Such a measuring task is already today performed radiometrically, typically with emitters provided in an immersion tube in the separator and the detectors fitted outside. Each detector is in this case typically calibrated in such a way that it measures the density of the material at the height of the detector. This is accomplished for example by each detector being assigned an emitter at the same height. The individual layers can then be inferred from the density profile.

It has, however, been recognized by the invention that, in particular in the case of round separator geometries, it is unavoidable that there is crosstalk from the various spot emitters into the other detectors. This crosstalk makes up a great part of the overall error of the system, since the densities can no longer be sharply spatially determined any longer. Although collimators can be used in this respect, they typically do not solve the problem completely. Even good calibration cannot eliminate the crosstalk, since the proportion of the crosstalk is dependent on the liquid levels above and below the detector.

The invention therefore addresses the problem of providing a method for measuring counting rates or measured variables dependent on the counting rates for determining a density profile that produces more accurate results. The invention also addresses the problem of providing an associated apparatus.

This is achieved by a method and an apparatus according to the claimed invention.

The invention relates to a method, in particular an automatic method, for measuring, in particular automatically measuring, counting rates or measured variables dependent on the counting rates, in particular proportional to the counting rates, for determining a density profile of at least two, in particular at least three, substances with different densities, in particular different values of the densities, which are arranged within a container, to be precise by using a plurality of detectors, in particular, gamma-energy-sensitive detectors. The method comprises the following steps:

a) in each case recording, in particular automatically and/or gamma energy-sensitively recording, respective gamma rays which have in each case penetrated at least partially through at least one of the substances, by using the detectors, and b) in each case generating, in particular automatically generating, a respective counting rate, in particular a value of the counting rate, or a respective measured variable dependent on, in particular proportional to, the counting rate, in particular a value of the measured variable, only or exclusively on the basis of respectively recorded gamma rays of which the respective gamma energy, in particular of which the respective gamma energy value, is greater than or equal to an energy threshold value, in particular and no less, the energy threshold value being a minimum of 0.5 times a Compton energy value of a Compton gap of the gamma rays, in particular the recorded gamma rays.

It can be achieved by the method according to embodiments of the invention that only gamma rays that still have a high energy level when they meet the detector enter the evaluation, it consequently being possible to assume that these gamma rays have not scattered, or only very little. Recognized effects of crosstalk in which gamma rays are emitted or emerge from radiation sources and, before meeting a detector, scatter so often that they no longer have any reasonable information content and have penetrated or passed through various layers can be effectively avoided in this way. By contrast, in the case of high-energy gamma rays that are evaluated according to embodiments of the invention, it can be assumed that they have not scattered, or at least only little, and therefore typically have only penetrated or passed through one layer, which they are also actually intended to measure. The information ascertained about the respective layer is correspondingly more accurate.

In a spectrum of a respective frequency, in particular counting rate, over a respective energy of gamma rays after penetrating or passing through a substance, a Compton gap is typically a gap directly below a peak that indicates the maximum energy, i.e. the energy corresponding to an emission energy or emergence energy from the radiation source. Only below the Compton gap, that is to say at lower energy levels than the maximum peak minus the Compton gap, do significant frequencies, in particular counting rates, occur again in the spectrum. Lying within the Compton gap is the Compton energy value, which typically can be defined as the energy value at a minimum frequency, in particular counting rate, within the Compton gap or else as the minimum of a fitted function, for example U-shaped function, within the Compton gap. As a result, in particular a delimitation is achieved between gamma rays that have not scattered, and consequently have an energy level above the Compton energy value, and gamma rays that have scattered, and consequently have an energy level below the Compton energy value.

No counting rate(s) or no measured variable(s) need or can be generated on the basis of respectively recorded gamma rays of which the respective gamma energy is less than the energy threshold value.

According to one embodiment, the method may comprise the following step: c) determining, in particular automatically determining, the density profile, in particular values of the density profile, on the basis of, in particular only, respectively generated counting rates or the respectively generated measured variables. In particular, the density profile need not or cannot be determined on the basis of (a) counting rate(s) or (a) measured variable(s) generated on the basis of respectively recorded gamma rays of which the respective gamma energy is less than the energy threshold value.

According to one embodiment, in step a), the recording may in each case comprise the following: in each case generating respective detector signal pulses by the detectors, with respective forms, in particular amplitudes and/or widths and/or products of the amplitudes and widths, of the respectively generated detector signal pulses being dependent on, in particular proportional to, the respective gamma energy levels of the respectively generated, in particular recorded, gamma rays. Step b) may comprise the following: in each case generating the respective counting rate or the respective measured variable only or exclusively on the basis of respectively generated detector signal pulses of which the respective forms are equal to or greater than a form threshold value, the form threshold value being dependent on the energy threshold value.

The form threshold value can be understood as meaning in particular an abstract threshold value which is defined on a scale that is indicative of a form. The use of forms and comparison with the form threshold value makes it possible in particular for gamma rays to be better detected, allowing for example events with an unusual form that are registered at the detector to be rejected. As a result, for example, the measurement can be restricted to events which are based on gamma rays that have penetrated or progressed in the desired way from a radiation source through a layer to a detector. In addition or as an alternative, the form threshold value may be an amplitude threshold value and/or a width threshold value and/or a product threshold value.

According to one embodiment, the detectors may have a detector noise with a noise energy value, the energy threshold value being a minimum of 2 times the noise energy value. This can achieve the effect that detector noise is automatically filtered out, presumed events that lie in the noise being filtered out on account of their energy being too low. In addition, consequently, the energy threshold value may be significantly above an energy threshold value, in particular a known energy threshold value, for filtering out detector noise, which permits frequently scattered gamma rays to enter the evaluation.

In additional or as an alternative, the energy threshold value may be a minimum of equal to the Compton energy value. It may in particular be equal to the Compton energy value. This can advantageously achieve the effect that only events with an energy level above the Compton gap are actually evaluated, and consequently the evaluation is restricted to gamma rays that pass through the substance respectively to be measured without scattering events.

According to one embodiment, the detectors may be arranged laterally outside a wall, in particular a round wall, of the container. In addition or as an alternative, the detectors may be arranged vertically one above the other. As a result, a good adaptation to the wall of the container can be achieved, it being possible for example with the round wall for the detectors to be arranged along a curved path, which may for example have a semicircular form.

According to one embodiment, the method may comprise the following step: in each case emitting respective gamma rays with a discrete isotope gamma energy, in particular a discrete isotope gamma energy value, into at least one of the substances by a plurality of radiation sources, the Compton energy value being less than the isotope gamma energy. Correspondingly emitted gamma rays may be used for the evaluation described here, and generally for measuring purposes.

According to a preferred embodiment, the radiation sources may be arranged within the container. As a result, the gamma rays emerging from the radiation sources directly enter the respective substance.

According to a preferred embodiment, the detectors may in each case be directed at an assigned radiation source. As a result, there is a direct assignment between detectors and radiation sources, it typically being desired that gamma rays emerging from a specific radiation source are only detected by one detector, typically after passing through a specific substance. As an alternative, the detectors may be directed at a point between, in particular midway between, two assigned radiation sources, whereby for example a "staggered" embodiment can be achieved.

According to a preferred embodiment, the detectors may be arranged in each case at the same height as the assigned radiation source. With an assumed horizontal alignment of the respective layers of substances, it can consequently be achieved in a preferred way that gamma rays that have not scattered have actually only passed through one substance before they reach the detector. As an alternative, the detectors may be arranged in each case at the same height as the point between the two assigned radiation sources.

According to one embodiment, the detectors may in each case comprise a collimator, the collimators respectively narrowing an angle of incidence, in particular in each case to the assigned radiation source(s). In addition or as an alternative, the radiation sources may in each case comprise a collimator, the collimators respectively narrowing an angle of reflection, in particular in each case to the assigned detector(s). As a result, a still better assignment between the detector and the radiation source(s) can be achieved, allowing in particular even further prevention of crosstalk, in particular of unscattered gammas, between detectors and radiation sources.

According to one embodiment, the detectors may in each case comprise a scintillator for recording respective gamma rays, the scintillators being able to comprise or have, in particular in each case, a density of a minimum of 3 grams per cubic centimeter ($g/cm^3$), in particular a minimum of 5 $g/cm^3$, and/or a maximum of 20 $g/cm^3$, in particular a maximum of 10 $g/cm^3$, in particular of 7 $g/cm^3$. In particular, the scintillators may partially or completely consist of elements with an atomic number (Z) of greater than or equal to 31, 39, 48, 53, 55 or 57. Such scintillators, in particular such elements, have proven to be advantageous for the detection purposes relevant here, in particular since there is a greater probability of the respective energy of gamma rays being completely deposited in them. In particular, bismuth germanate (BiGeO) and/or lanthanum bromide (LaBr) and/or cesium iodide (CsI) and/or lutetium yttrium oxyorthosilicate (LuYSiO) and/or cadmium tungstate (CdWo) and/or gadolinium aluminum gallium oxide (GdAlGaO) can be used. They may for example be used in a respective detector on their own or else in combination.

According to one embodiment, the substances may comprise or be gas, foam, oil, emulsion, water and/or sand. In addition or as an alternative, the container may be an oil-water separator. Also in addition or as an alternative, the substances may comprise or be gas, hydrocarbon and/or acid. Also in addition or as an alternative, the container may be a hydro-carbon-acid separator. The method according to embodiments of the invention has proven to be particularly advantageous for such applications. In particular, gas may refer to air and/or hydrocarbons. In addition or as an alternative, foam may refer to a gas-oil mixture. Also in addition or as an alternative, emulsion may refer to an oil-water mixture.

The invention also relates to an apparatus for measuring counting rates, in particular the counting rates, or measured variables, in particular the measured variables, dependent on, in particular proportional to, the counting rates for determining a density profile, in particular the density profile, of, in particular the, at least two, in particular at least three, substances with different densities arranged within a container, in particular the container, by a plurality of detectors, in particular the plurality of detectors. In particular, the apparatus may be designed for performing a method according to the invention, it being possible to take all of the embodiments and variants described here as a basis again.

The apparatus comprises a plurality of detectors, in particular electrical detectors, the detectors being designed or configured in each case for recording respective gamma rays which have in each case penetrated at least partially through at least one of the substances. The apparatus has a plurality of generating devices, in particular electrical generating devices, the generating devices being designed or configured in each case for generating a respective counting rate or a respective measured variable dependent on, in particular proportional to, the counting rate only on the basis of respectively recorded gamma rays of which the respective gamma energy is greater than or equal to an energy threshold value, the energy threshold value being a minimum of 0.5 times a Compton energy value of a Compton gap of the gamma rays, in particular the recorded gamma rays.

By way of such an apparatus, in particular the method according to embodiments of the invention can be carried out, and the advantages already described further above can be achieved. With respect to the apparatus, it is possible to take all of the variants described here with respect to the method according to the invention as a basis again.

The generating devices need not or cannot generate any counting rate(s) or measured variable(s) on the basis of respectively recorded gamma rays of which the respective gamma energy is less than the energy threshold value.

According to one embodiment, the apparatus may comprise a determining device, the determining device being designed or configured for determining the density profile on the basis of, in particular only, the respectively generated counting rates or the respectively generated measured variables. The determining device may also be designed to perform the method according to embodiments of the invention. This allows an advantageous evaluation as already described further above to be achieved. In particular, the determining device need not or cannot determine the density profile on the basis of (a) counting rate(s) or (a) measured variable(s) generated on the basis of respectively recorded gamma rays of which the respective gamma energy is less than the energy threshold value.

According to one embodiment, the apparatus may comprise a plurality of radiation sources, the radiation sources being designed or configured in each case for emitting respective gamma rays with a discrete isotope gamma energy into at least one of the substances, the Compton energy value being less than the isotope gamma energy. In addition or as an alternative, the apparatus may comprise the container.

Instead of a substance, it is also possible for example to speak of a material.

The density profile may be in particular a vertical density profile, i.e. the density may change along a vertical direction, in particular on account of a separation by way of gravitation. Layers of mixtures of gas, liquid and/or solid matter may be formed for example.

It should be mentioned that, in addition to the evaluations already described here, further evaluations, such as for example those with respect to a temperature, are also possible. As a result, the measuring accuracy can be improved further.

The energy threshold value may for example have the same value for all detectors, but different values may also be used.

The detectors may in particular be of the same type of construction, but they may also be differently formed.

It should be mentioned that, for example, two, three, four or five detectors may be used. More detectors may also be used.

It should be mentioned that isotopes used in radiation sources may also have not only one energy level but for example also two discrete energy levels. In particular, the energy threshold value may be chosen or set on the basis of the higher discrete energy level. In addition or as an alternative, the two discrete energy levels may be so close to one another that they can be treated as one discrete energy level with respect to the energy threshold value, such as for example for cobalt-60. Mixed isotopes may also be used.

The detectors may for example comprise in each case a photomultiplier, in particular a silicon photomultiplier.

In the scintillator, if present, gamma rays may in each case trigger multiple flashes of light, the number of which depends on the energy of the respective gamma rays. These very weak flashes of light may release electrons from a photocathode of a photomultiplier fitted downstream, if present. These electrons may be multiplied in an avalanche-like manner by instances of impact with electrodes in the photomultiplier. A current pulse that can be measured well, in particular the amplitude of which may be dependent on the energy of the respective gamma rays, can then be picked up at an anode. In the case of particularly compact scintillation counters, a sensitive photodiode may also be used instead of the photomultiplier. For example, an optoelectronic sensor may be used.

Further advantages and aspects of the invention are evident from the claims and from the following description of preferred exemplary embodiments of the invention which are explained below with reference to the figures.

BRIEF DESCRIPTION OF THE DRAWINGS

FIG. 3 shows a schematic view of the apparatus from FIG. 1 and of the method from FIG. 2.

FIG. 4 shows a further schematic view of the apparatus from FIG. 1.

DETAILED DESCRIPTION OF THE DRAWINGS

FIGS. 1 to 6 show a method according to an embodiment of the invention and an apparatus 10 according to an embodiment of the invention for measuring counting rates ZR1, ZR2, ZR3, ZR4 for determining a density profile DP of at least two substances ST with different densities DE arranged within a container 20 by using a plurality of detectors 41, 42, 43, 44.

Figure 1:
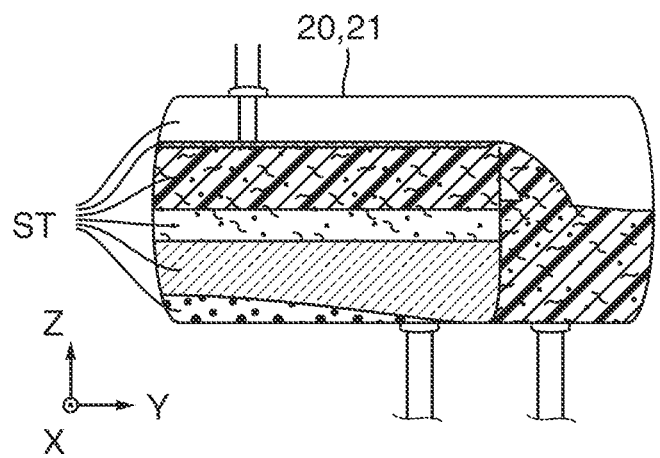
FIG. 1 shows a longitudinal sectional view of an apparatus according to embodiments of the invention comprising a container.

In detail, the apparatus 10 comprises the container 20, which in the present case is designed as an oil-water separator 21. In this case, the substances ST lie one above the other in a layered manner. The container 20 serves in principle for separating these substances ST. Also depicted in FIG. 1 is a coordinate system, which defines an x axis, y axis and z axis.

Figure 2:
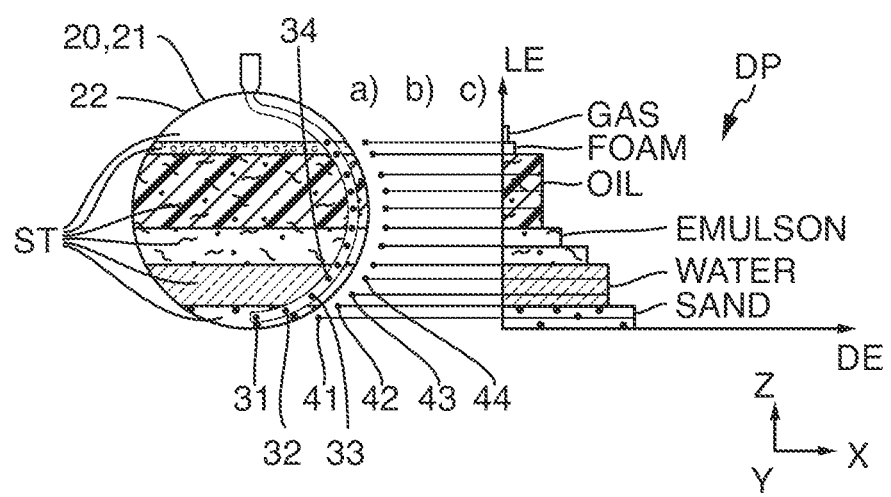
FIG. 2 shows a cross-sectional view of the apparatus from FIG. 1 and of a method according to embodiments of the invention.
Figure 6:
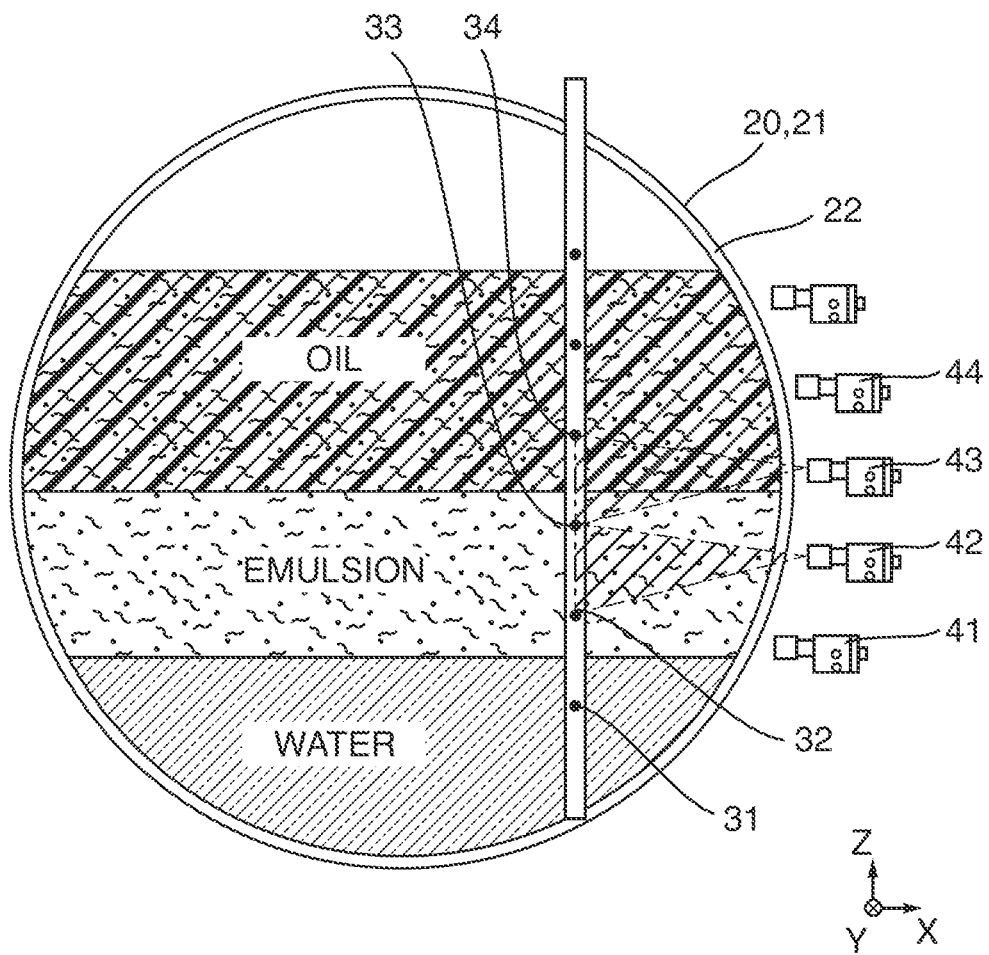
FIG. 6 shows a further embodiment of the apparatus from FIG. 1.

FIGS. 2 and 6 show the container 20 in cross section with the substances ST located in it and a list alongside of the various substances ST. It can be seen here that the container 20 has a round cross section. This is defined by a wall 22.

The substances ST or the discernible layers in the container 20 are in the present case, from bottom to top or in the z direction, sand (SAND), water (WATER), an emulsion (EMULSION), oil (OIL), foam (FOAM) and gas (GAS). It should be understood that such substances ST are only given by way of example.

Arranged within the container 20 are a plurality of radiation sources 31, 32, 33, 34 of the apparatus 10, only some of which are schematically denoted here. As shown in FIGS. 2 to 4, the radiation sources 31, 32, 33, 34 are arranged vertically one above the other or in the z direction along an arcuate segment and have in each case, as seen in the radial x direction, a similar distance from the wall 22. Arranged on the right side in relation to the, in particular round, wall 22 or outside the container 20 in the x direction are a plurality of detectors 41, 42, 43, 44 of the apparatus 10, only some of which are schematically denoted here. These are also arranged vertically one above the other or in the z direction along an arcuate segment. Consequently, in a step a) of the method, the detectors 41, 42, 43, 44 may in each case record respective gamma rays GR, which have in each case been emitted by the radiation sources 31, 32, 33, 34 and have penetrated at least partially through the respective substance ST.

Shown on the right in FIG. 2 is the density profile DP of the substances ST. In this case, the respective density DE of one of the substances ST is indicated over the height LE. It can be seen that, in principle, the density DE increases from top to bottom or counter to the z direction and the substances ST are correspondingly separated.

FIG. 3 shows in detail mechanisms for the evaluation and an associated schematic signal processing. In this case, only the four detectors 41, 42, 43, 44 already mentioned and the assigned radiation sources 31, 32, 33, 34 are shown, as representative of the total number of detectors and radiation sources.

Figure 5:
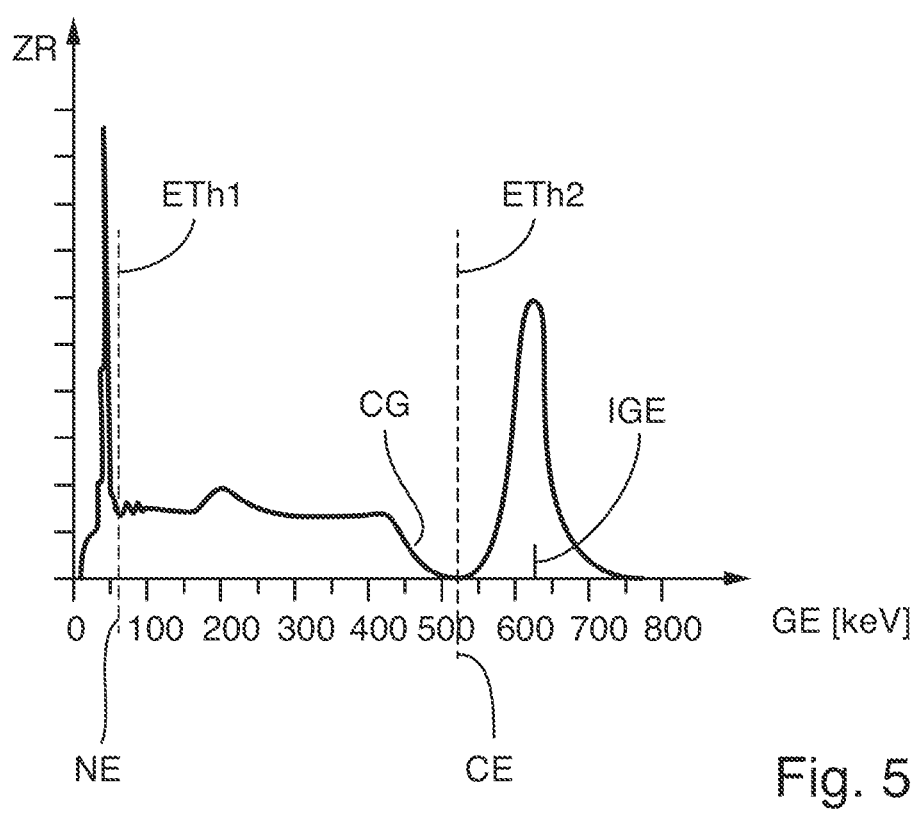
FIG. 5 shows an energy spectrum of gamma rays.

By using a plurality of generating devices 71, 72, 73, 74 of the apparatus 10, in a step b) of the method, respective counting rates ZR1, ZR2, ZR3, ZR4 are only generated on the basis of respectively recorded gamma rays GR of which the respective gamma energy GE is equal to or greater than an energy threshold value ETh2, the energy threshold value ETh2 being a minimum of 0.5 times a Compton energy value CE of a Compton gap CG of the gamma rays GR, in particular the recorded gamma rays GR, as shown in FIG. 5.

In detail, in step a), the detectors 41, 42, 43, 44 in each case generate respective detector signal pulses DI1, DI2, DI3, DI4, with respective forms, in particular amplitudes IA1, IA2, IA3, IA4, of the respectively generated detector signal pulses DI1, DI2, DI3, DI4 being dependent on the respective gamma energy levels GE of the respective gamma rays GR, in particular recorded gamma rays GR. In this case, in particular respective forms, in particular amplitudes IA1, IA2, IA3, IA4, of the respectively generated detector signal pulses DI1, DI2, DI3, DI4 are evaluated. The respective forms, in particular the respective amplitudes IA1, IA2, IA3, IA4, are in each case compared with a respective form threshold value ATh2, the form threshold value ATh2 being dependent on the energy threshold value ETh2. The respective counting rates ZR1, ZR2, ZR3, ZR4 are only generated and evaluated on the basis of respectively generated detector signal pulses DI1, DI2, DI3, DI4 or events of which the respective forms, in particular their respective amplitudes IA1, IA2, IA3, IA4, are greater than or equal to the form threshold value ATh2.

In the present case, the energy threshold value ETh2 is equal to the Compton energy value CE of the Compton gap CG of the gamma rays GR used, that is to say the gamma rays GR emitted by the radiation sources 31, 32, 33, 34.

On the basis of the counting rates ZR1, ZR2, ZR3, ZR4, the density profile DP is subsequently determined in a step c) of the method by a determining device 80 of the apparatus 10.

As a result, a respective density DE between the respective radiation source 31, 32, 33, 34 and the respective detector 41, 42, 43, 44 can be advantageously determined, since almost exclusively unscattered gamma rays GR are evaluated. Crosstalk effects are thereby avoided.

The effect of crosstalk is shown in FIG. 3. Depicted there, specifically by a respective solid line, are respective gamma rays GR which run directly horizontally from the respective radiation source 31, 32, 33, 34 to the respective detector 41, 42, 43, 44. Also depicted however, by dashed lines, are radiation profiles of gamma rays GR that represent crosstalk. Such gamma rays GR are typically undesired for the evaluation, since they have been scattered and typically have not only penetrated through one substance ST. Consequently, they do not contribute to reliable density determination. This effect is particularly strong in the case of round geometries, but also occurs in the case of other geometries.

FIG. 4 shows part of the apparatus 10, the specific mechanisms for the evaluation no longer being represented. The detectors 41, 42, 43, 44 comprise respective collimators 51, 52, 53, 54, which ensure that an angle of incidence or recording angle EW of the respective detector 41, 42, 43, 44 is narrowed, in particular to the respectively assigned radiation source 31, 32, 33, 34. In addition, the radiation sources 31, 32, 33, 34 comprise respective collimators 81, 82, 83, 84, which ensure that an angle of reflection AW of the respective radiation source 31, 32, 33, 34 is narrowed, in particular to the respectively assigned detector 41, 42, 43, 44. Although this allows crosstalk effects to be reduced, they cannot be avoided completely, as can be easily seen for example from a possible profile, depicted by dashed lines, of a multiply scattered gamma ray or gamma quant GR.

The respective angle of incidence is in this case represented by the reference sign EW, specifically by way of example in the case of the lowermost detector 41. The respective angle of reflection is in this case represented by the reference sign AW, specifically by way of example in the case of the uppermost radiation source 34.

The detectors 41, 42, 43, 44 comprise in each case a scintillator 61, 62, 63, 64 for recording respective gamma rays GR, in particular which respond to incident gamma rays GR by giving off respective flashes of light. These flashes of light are then typically intensified by photomultipliers and correspondingly evaluated. The scintillators 61, 62, 63, 64 may have a density of a minimum of 3 g/cm$^3$ and/or a maximum of 20 g/cm$^3$. As shown, the scintillators 61, 62,

63, 64 may partially or completely consist for example of an element with a high atomic number Z, in particular greater than or equal to 31, it being possible for example for BiGeO, LaBr, CsI, LuYSiO, CdWO or GdAlGaO to be used.

FIG. 5 shows a typical energy spectrum that is detected by one of the detectors 31, 32, 33, 34. On the horizontal axis, the respective energy GE of the gamma rays GR is indicated here in the unit keV, on the vertical axis the respective counting rate ZR is indicated for each energy level or energy channel.

At low energy levels, initially electronic noise is evident, lying below another energy threshold value ETh1. The noise ends at the noise energy value NE.

In the exemplary embodiment shown, when using cesium-137 (Cs 137) for the radiation sources 31, 32, 33, 34, the Compton gap CG, in which the counting rate ZR becomes virtually zero, is arranged between approximately 450 keV and 600 keV. In the middle of this Compton gap CG is the Compton energy value CE, which in the present case is equal to the energy threshold value ETh2. Above it is a peak with a distinct maximum for a discrete isotope gamma energy IGE of the emitted gamma rays GR from the radiation sources 31, 32, 33, 34. In other words: the Compton energy value CE is less than the isotope gamma energy IGE. In alternative exemplary embodiments, the detectors may in each case comprise a scintillator, in particular an organic scintillator, by way of which a detected energy spectrum comprises or has a less distinct peak or no peak for a discrete isotope gamma energy. To put it another way: a significant frequency, in particular counting rate, may end with the Compton gap.

If the other energy threshold value ETh1 were used in the exemplary embodiment shown, it would detect all of the gamma rays GR that lie at or above the noise threshold. This may lead to the undesired effects already described further above, since in particular gamma rays GR that have been multiply scattered and have passed through layers that are not to be measured at all are also detected. If, on the other hand, the energy threshold value ETh2, which is in particular a minimum of 2 times the noise energy value NE, is used, only evaluated are the unscattered gamma rays GR which have typically only passed horizontally through one substance ST, for example with the arrangement described with respect to FIGS. 2 to 4. These typically have the full energy of the radiation sources 31, 32, 33, 34, which for example when using cesium-137 has a value of 662 keV. With this selection, for example supported by the use of collimators 51, 52, 53, 54, 81, 82, 83, 84, gamma rays or gamma quants GR that have arrived at one of the detectors 41, 42, 43, 44 after at least one scattering are also filtered out, so that in any event there is a good assignment in each case between the radiation sources 31, 32, 33, 34 and the detectors 41, 42, 43, 44. This makes a significantly improved measurement result possible, which in turn makes it possible that an installation can be operated much closer to the design limit, without for example in case of the oil-water separator 21 running the risk of untreated oil leaking out into the waste water.

The properties of Compton scattering are known in principle, so that the energy loss of the gamma rays GR can be directly attributed to a scattering angle. However, this conversely also allows scatterings that have only taken place at a small angle, and consequently have not yet put at risk the respective assignment of radiation sources 31, 32, 33, 34 and detectors 41, 42, 43, 44, to continue to be permitted. This is possible by not setting the measurement threshold directly below the peak with maximum energy, but further below that. The further down the threshold can be brought, the more scattered gamma rays GR are detected. This provides a way of adjustment between allowed crosstalk (=measuring accuracy) and counting rate efficiency. The solution according to embodiments of the invention can therefore be optimized and adapted according to the application.

Since the gamma rays or gamma quants GR in the respective scintillators 61, 62, 63, 64 are detected both by way of the photo effect and by way of the Compton scattering, it may be that even gamma rays GR with full energy IGE could only deposit a fraction of the energy IGE in the respective scintillator 61, 62, 63, 64. As a result, they would be falsely detected as gamma rays GR with too low energy. This effect can be countered by using the detector material with a high density, in particular with elements with a high atomic number Z. Then the photo effect outweighs the Compton scattering, whereby the full energy, in particular IGE, is detected. The low counting rate efficiency can also be compensated by increasing the source activity. Often, however, it may also be sufficient to increase the averaging time, since the processes in separators do not in any case proceed quickly.

FIG. 6 shows another alternative configuration of the container 20 with the radiation sources 31, 32, 33, 34 and detectors 41, 42, 43, 44. As a difference from the embodiment of FIGS. 2 to 4, the detectors 41, 42, 43, 44 are no longer directed here in each case at an assigned radiation source 31, 32, 33, 34, in particular arranged at the same height in the z direction as the associated radiation source 31, 32, 33, 34, but are rather directed at a point between, in particular midway between, two assigned radiation sources 31, 32, 33, 34, in particular arranged at the same height in the direction z as the point between the two assigned radiation sources 31, 32, 33, 34, or offset thereto as seen in the z direction.

What is claimed is:

1. A method for measuring counting rates or measured variables dependent on the counting rates for determining a density profile of at least two substances with different densities arranged within a container by using a plurality of detectors, the method comprising, in each case:
    emitting respective gamma rays with a discrete isotope gamma energy into at least one of the substances by using a plurality of radiation sources, wherein a Compton energy value is less than the isotope gamma energy,
    recording the respective gamma rays which have penetrated at least partially through at least one of the substances by using the plurality of detectors, and
    generating a respective counting rate or a respective measured variable dependent on the counting rate only on the basis of respectively recorded gamma rays of which the respective gamma energy is greater than or equal to an energy threshold value, the energy threshold value being a minimum of 0.5 times the Compton energy value of a Compton gap of the gamma rays.

2. The method according to claim 1, further comprising: determining the density profile on the basis of the respectively generated counting rates or the respectively generated measured variables.

3. The method according to claim 1, wherein:
    recording the respective gamma rays comprises generating respective detector signal pulses by using the plurality of detectors, with respective forms of the respectively generated recorded detector signal pulses being dependent on respective gamma energy levels of the respectively recorded gamma rays, and
    the respective counting rate or the respective measured variable is generated only on the basis of respectively generated detector signal pulses of which the respective forms are equal to or greater than a form threshold value, the form threshold value being dependent on the energy threshold value.

4. The method according to claim 3, wherein the forms comprise at least one of amplitudes, widths, or products of the amplitudes and the widths.

5. The method according to claim 1, wherein at least one of:
the plurality of detectors have a detector noise with a noise energy value, and the energy threshold value is a minimum of 2 times the noise energy value, or
the energy threshold value is a minimum of equal to the Compton energy value.

6. The method according to claim 1, wherein at least one of:
the plurality of detectors are arranged laterally outside a round wall of the container, or
the plurality of detectors are arranged vertically one above the other.

7. The method according to claim 1, wherein:
the radiation sources are arranged within the container.

8. The method according to claim 1, wherein:
each of the plurality of detectors is directed at an assigned radiation source or at a point midway between two assigned radiation sources.

9. The method according to claim 8, wherein:
each of the detectors is arranged at a same height as the assigned radiation source or at a same height as the point midway between the two assigned radiation sources.

10. The method according to claim 1, wherein at least one of:
each of the plurality of detectors comprises a collimator, and each of the collimators respectively narrows an angle of incidence to an assigned radiation source, or
each of the radiation sources comprises a collimator, and each of the collimators respectively narrows an angle of reflection to an assigned detector.

11. The method according to claim 1,
each of the plurality of detectors comprises a scintillator for recording respective gamma rays, and each of the scintillators comprises a density of at least 3 g/cm³.

12. The method according to claim 1, wherein at least one of:
the substances comprise at least one of gas, foam, oil, emulsion, water, or sand,
the container is an oil-water separator,
the substances comprise at least one of hydrocarbon or acid, or
the container is a hydrocarbon-acid separator.

13. An apparatus for measuring counting rates or measured variables dependent on the counting rates for determining a density profile of at least two substances with different densities arranged within a container, the apparatus comprising:
a plurality of radiation sources, wherein each of the plurality of radiation sources is configured to emit respective gamma rays with a discrete isotope gamma energy into at least one of the substances, a Compton energy value being less than the isotope gamma energy;
a plurality of detectors, wherein each of the plurality of detectors is configured to record the respective gamma rays which have penetrated at least partially through at least one of the substances, and
a plurality of generating devices, wherein each of the plurality of generating devices is configured to generate a respective counting rate or a respective measured variable dependent on the counting rate only on the basis of respectively recorded gamma rays of which the respective gamma energy is greater than or equal to an energy threshold value, the energy threshold value being a minimum of 0.5 times the Compton energy value of a Compton gap of the gamma rays.

14. The apparatus according to claim 13, further comprising:
a determining device configured to determine the density profile on the basis of the respectively generated counting rates or the respectively generated measured variables.

15. The apparatus according to claim 13, further comprising:
the container.

* * * * *